United States Patent [19]

Groves et al.

[11] 4,298,836
[45] Nov. 3, 1981

[54] PARTICLE SHAPE DETERMINATION

[75] Inventors: Michael R. Groves, Miami; Wallace H. Coulter, Miami Springs, both of Fla.

[73] Assignee: Coulter Electronics, Inc., Hialeah, Fla.

[21] Appl. No.: 96,945

[22] Filed: Nov. 23, 1979

[51] Int. Cl.³ .......................................... G01N 27/00
[52] U.S. Cl. .......................... 324/71 CP; 73/432 PS
[58] Field of Search .......................... 324/64, 71 CP; 73/432 PS; 235/92 PC

[56] References Cited

U.S. PATENT DOCUMENTS

| | | |
|---|---|---|
| 2,656,508 | 10/1953 | Coulter . |
| 3,502,973 | 3/1970 | Coulter et al. . |
| 3,502,974 | 3/1970 | Coulter et al. . |
| 3,710,933 | 1/1973 | Fulwyler et al. . |
| 3,793,587 | 2/1974 | Thom . |
| 3,890,568 | 6/1975 | Coulter . |
| 3,941,479 | 3/1976 | Whitehead ............ 324/71 CP |
| 4,165,484 | 8/1979 | Haynes ............ 324/71 CP |
| 4,198,160 | 4/1980 | Kachel ............ 324/71 CP |
| 4,224,567 | 9/1980 | Hoffman ............ 324/71 CP |

OTHER PUBLICATIONS

Kay et al., "Imaging in Flow", Jour. of Histochemistry and Cytochemistry, vol. 27, No. 1, pp. 329-334.
Kachel et al., "Fast Imaging in Flow: A Means of Combining Flow-Cytometry and Image Analysis", Journal of Histochemistry and Cytochemistry, vol. 27, No. 1, pp. 335-341, 1979.

Primary Examiner—Michael J. Tokar
Attorney, Agent, or Firm—William A. Newton

[57] ABSTRACT

Apparatus and method wherein particles in a liquid stream are hydrodynamically focused to pass through an impedance sensing orifice, a low frequency current source provides a current through the orifice to produce a signal representative of the particle's size, a high frequency source provides a current through the orifice to produce a signal representative of the particle's size and internal resistance, a detector determines the particle's length, and a digital computer correlates the signals for each particle and calculates its shape factor, degree of deformation or natural shape, true volume and internal resistivity.

14 Claims, 2 Drawing Figures

U.S. Patent
Nov. 3, 1981
4,298,836
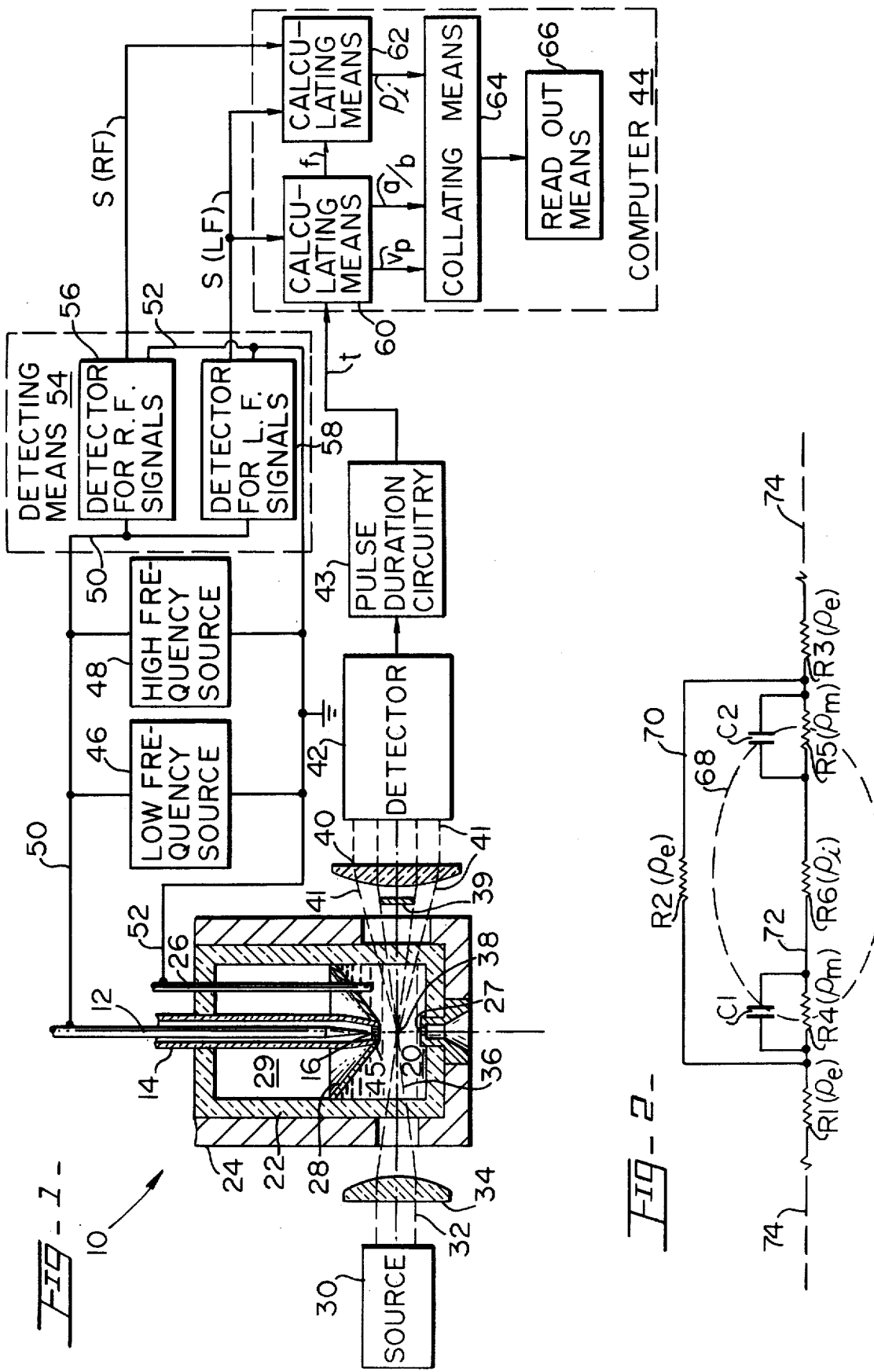

PARTICLE SHAPE DETERMINATION

FIELD OF THE INVENTION

The invention relates generally to particle analyzing apparatus and more particularly is concerned with apparatuses in which studies may be made of particulate systems using the impedance sensing principle.

BACKGROUND OF THE INVENTION

Since its conception more than 25 years ago, the principle of particle counting and sizing invented by Wallace H. Coulter has resulted in numerous methods and apparatuses for the electronic counting, sizing and analysis of microscopic particles, which are scanned in a fluid suspension, as shown by the pioneer U.S. Pat. No. 2,656,508 to Coulter. In this prior art arrangement, a D.C. electric current flow is established between two vessels by suspending electrodes in the respective bodies of the suspension fluid. The only fluid connection between the two bodies is through an orifice; hence, an electric current flow and field are established in the orifice. The orifice and the resultant electric field in and around it constitute a sensing zone. As each particle passes through the sensing zone, for the duration of the passage, the impedance of the contents of the sensing zones will change, thereby modulating the current flow and electric field in the sensing zone, and hence causing the generation of a signal to be applied to a detector suitably arranged to respond to such change. (The mark "Coulter" is a registered trademark, Registration No. 995,825, of Coulter Electronics, Inc. of Hialeah, Florida.)

It has been proven that the change in impedance of the contents of the sensing zone as a particle passes through it is approximately proportional to the volume of the particle, where the cross-sectional area of the particle is substantially smaller than the cross-sectional area of the orifice, and the particle is smaller in diameter than the axial length of the orifice. Accordingly, numerous embodiments of commercial particle analyzers have been developed which measure signal amplitude output of an impedance sensing arrangement, for the purpose of measuring particle volume or size of the particles. Such an arrangement measures the electrical size of the particle which will be hereinafter referred to as "particle size" or "measured size".

It has also been proven that the particle's shape affects the measured size so that it does not correlate exactly with the actual or true volume of the particle. Generally, due to the hydrodynamic focusing in most apparatuses, elongated particles will be aligned with their elongated axis substantially parallel to the center axis of the orifice. With two equal volume particles, one being spherical and one being elongated, the spherical particle, while passing through the orifice, will have a greater cross section perpendicular to the current flow than the elongated particle. Hence, the spherical particle will distort the field in such a manner that it will give a greater measured size than the elongated particle, despite their equal volumes. To compensate for this, particles have been classified as to their shape by a term called "shape factor". For instance, if an extremely elongated particle is assigned a shape factor of 1.0, then the spherical particle of the same volume has a shape factor of 1.5. An apparatus using two sensing orifices capable of determining shape factor is shown in U.S. Pat. No. 3,793,587 to Thom et al. In this device, the length of one of the orifices has the same order of magnitude of the particle lengths or is smaller than the particle lengths. Consequently, with this orifice, an elongated particle causes a pulse, which after rising, remains at a maximum for a certain length of time and then falls. A spherical particle produces, in contrast, a pulse that falls immediately after reaching a maximum. In this patent it is suggested that the measured size can be corrected by dividing the impedance change for a particle by its shape factor. Due to complications of electric fields, these corrections leave much room for improvement.

Particle deformability, caused by hydrodynamic pressures as the particle proceeds through a sensing orifice, or particle shape can be very important, both as a factor affecting measured size and as a separate parameter for examining particles. First, the deformation or shape of the particles affects their shape factor, which in turn affects the measured size. Secondly, the deformed state of a biological cell depends not only upon the type of cell, but upon the age of the cell. For instance, mammalian erythrocytes have no nucleus. In contrast to leukocytes, the erythrocytes are easily deformable, due to their low inner viscosity. Also, within a given type of cell, the cell membrane becomes more rigid with age, therefore less deformable. It is contemplated that the pathological state of a cell will affect its deformability or natural shape.

In the commercial apparatus constructed in accordance with the heretofore mentioned U.S. Pat. No. 2,656,508, field excitation has been supplied by a direct current or low frequency source. As previously described, the electrical change caused by the passage of a particle through the electric field of small dimensions, excited by a direct or low frequency current, is approximately proportional to particle size. A direct current is considered to be of zero frequency in this application. However, the impedance sensing principle has been materially expanded to provide information concerning particles being studied, not limited only to characteristics due to the size of particles, but including characteristics due to the composition and nature of the material constituting the particles, as disclosed in U.S. Pat. No. 3,502,974 to Coulter et al. and U.S. Pat. No. 3,502,973 to Coulter et al. These prior art apparatuses generally have at least two current sources, both of which are applied to the sensing zone simultaneously, one having a radio frequency and the other being a "zero frequency" direct current or, alternatively, having a sufficiently low frequency that the reactive part of the particle impedance has a neglible effect on the response of the apparatus. One of the useful particle descriptors that can be obtained from this dual source arrangement is known in the art as the "opacity" of the particles. In a general sense, opacity measures the difference in size as measured at radio frequency as compared to size measured at low or zero frequency.

As is appreciated in the art of cytology, any new particle descriptor that can be measured is useful in identifying, analyzing and sorting particles. For example, cells have a membrane of very high resistivity which is in the range of a dielectric. However, the internal portion of the cell is fairly conductive, with different types of particles having varying internal resistivities. Also, it is contemplated that the pathological state of the cell will affect its internal resistivity. Consequently, it is desirable to measure this internal resistivity on a cell by cell basis.

U.S. Pat. No. 3,890,568 to Coulter et al. is of interest in that it discloses the electrical field configuration for an illustrative sensing orifice. Moreover, this patent teaches the measurement of particle length for the purpose of correcting inaccurate size measurements caused by elongated particles which exceeded the length of the sensing zone. However, the procedure disclosed therein is capable of accurately determining length of the particle only when the particle's length exceeds the effective scanning ambit, or to put it another way, the range within which the particle can be effectively sensed. This situation generally occurs only in instances when such particles as fibers are being sorted. With most particles, such as biological cells, the length of the orifice will be several times the length of the particles, even when the particles are stretched by the hydrodynamic forces involved.

The device disclosed in an article entitled "Fast Imaging in Flow: A Means of Combining Flow-Cytometry and Image Analysis", V. Kachel et al., THE JOURNAL OF HISTOCHEMISTRY AND CYTOCHEMISTRY, Vol. 27, No. 1, (1979), pp. 335–341, is of interest for disclosing a prior art scheme that is capable of subsequent examination of particle shape, after the particle has passed through a sensing orifice. In this device, an electronic unit associated with the sensing orifice, for a limited, preselected subpopulation of cells, triggers a flashlamp to project images of the selected cells on a film, for subsequent storage and examination. However, this arrangement has no capability of correlating particle shape with measured volume on a particle by particle basis. Shape information cannot be readily quantified in a rapid manner for computer processing, since its final form is nothing more than an image on the film. Moreover, flow speeds are limited to 5 meters per second with a maximum of only 150 pictures being taken per second, and then only for particles that are preselected. Typical flow speeds are 5 to 10 meters per second with a particle count rate of 1,000 to 5,000 particles per second.

An impedance sensing orifice has been used in combination with downstream light absorbance detection, scattered light detection and fluorescent light detection, as disclosed in U.S. Pat. No. 3,710,933 to Fulwyler et al. However, the types of optical measurements made downstream from the orifice do not provide the information required for the hereinafter described invention. Other prior art arrangements have simultaneously measured impedance and the above mentioned optical signals in optically clear flow cells. Although scattered light patterns are affected by particle shape, this effect is detectable and discernible only by extremely complex apparatus with marginal accuracy, since it is masked by scattered light created by reflected light, which is primarily dependent upon particle size, and refracted light, which is primarily dependent upon the particle's light transmission characteristics, namely absorption and refractive index, and size.

Various slit scanning techniques for analyzing particles with a narrow beam of light are known in the art, as illustrated by an article entitled "Imaging in Flow", D. B. Kay et al., published by THE JOURNAL OF HISTOCHEMISTRY AND CYTOCHEMISTRY, Vol. 27, No. 1, (1979), pp. 329–334.

SUMMARY OF THE INVENTION

The invention is directed toward a particle scanning apparatus and method wherein particles suspended in a liquid stream are hydrodynamically focused to pass through an impedance sensing orifice. A low frequency current source provides a current through the orifice to produce a first impedance signal, which is approximately representative of the particle's size. A high frequency current source provides a current through the orifice to produce a second impedance signal, which is primarily representative of the internal resistance of the particle, which is in turn dependent upon particle's size, shape, orientation and internal resistivity. A detection means provides an electrical time of flight signal representative of the length of each particle, which is used to correct the size measurement inherent in the first impedance signal to give accurate shape and volume measurements, which are essentially independent of particle shape. With the accurate shape and volume measurements, a precise determination of a particle's resistivity can be extracted from the internal resistance measurements inherent in the second impedance signal. The determination of a particle's resistivity on a particle-by-particle basis is of great value as a new descriptor for analyzing and identifying biological cells.

In the prior art devices, it was possible to use the second impedance signal to measure the particle's internal resistance, but this measurement has no meaning by itself. This is due to the fact that internal resistance measurement varies not only with the particle's internal resistivity, but also with the size, the shape, and the orientation of the particle. Likewise, in the prior art devices, it was possible to use the first and second impedance signals to measure the particle's opacity, but this measurement has no direct interpretation by itself. This is due to the fact that the opacity measurement varies substantially with the shape, the orientation and the internal resistivity of the particle. The apparatus and method of the invention provide the elongated particles with the same orientation along a predetermined trajectory during all signal generation. Then, the novel combination of the three generated signals allows for the accurate extraction of the internal resistivity of particles, which heretofore was unobtainable by any prior art flow system. Hence, a valuable new particle descriptor has been made available to the art of cytology through this invention.

A novel subcombination of the apparatus and method of the invention utilizes an optical detector means for determining particle's time of flight, and therefore the particle's length. This novel subcombination has utility for measuring the shape factor, the true volume, and the deformed or natural shape of the particles on a particle-by-particle basis, by using only the first impedance signal and time of flight signal.

BRIEF DESCRIPTION OF THE DRAWINGS

Further objects and advantages of the present invention will become apparent as the following description proceeds, taken in conjunction with the accompanying drawings in which:

FIG. 1 is a part cross-sectional side view and part schematic diagram of the apparatus of the invention.

FIG. 2 is a schematic diagram of the electrical characteristics of a biological cell and the liquid suspending the cell.

DESCRIPTION OF THE PREFERRED EMBODIMENT

FIG. 1 illustrates a particle scanning apparatus 10 having a sample introduction tube 12, a sheath tube 14 positioned in surrounding, coaxial relationship to the tube 12, and a microscopic orifice 16 positioned at the end of the sheath tube 14. A liquid stream of individually suspended particles, originally from a pressurized reservoir (not shown), proceeds through the tube 12. A laminar liquid sheath, originally from another pressurized reservoir (not shown), proceeds through the tube 14 so as to surround the stream of particles. As the liquid stream of particles exits from the tube 12, hydrodynamic pressures reduce the diameter of the stream of particles as the stream obtains the velocity of the liquid sheath. The liquid sheath also acts to center the stream of particles so that particles pass through the orifice 16 along a center axis 18, with the elongated particles, if any, having their elongated axis aligned with the center axis 18. After leaving the orifice 16, the particles enter a liquid-filled flow chamber 20, which is defined in part by an optically clear cuvette 22. The optically clear cuvette 22 is surrounded by a metal housing 24. Preferably, the flow chamber 20 contains a second sheath liquid provided by a metal inlet tube 26. Due to the pressure drop associated with the orifice 16, it is desirable to have a second liquid sheath to provide sufficient hydrodynamic pressures to keep the elongated axis of the particles, if any, aligned with the center axis 18 and to pass the particles through the flow chamber 20 and an exit nozzle 27. If the particles are deformed while passing through the orifice 16, the second liquid sheath assists in providing the necessary hydrodynamic forces for maintaining the same degree of deformation during subsequent optical measurement, to be described hereinafter. This particle scanning arrangement as described above is of a conventional design and is shown in detail in U.S. Pat. No. 3,710,933 to Fulwyler et al. This arrangement is modified slightly by the inclusion of a fluid retarding partition 28, which separates the liquid-filled chamber 20 from an air filled chamber 29. Although the particles are shown passing along the center axis 18, other trajectories are possible. For instance, the stream of particles can be introduced along a predetermined trajectory which passes through the orifice 16 and forms an angle with the center axis 18. The important common feature of all possible trajectories is that the hydrodynamic pressure keeps the elongated axis of the particles consistently aligned with the predetermined trajectory, whether or not that trajectory is the center axis 18.

A light source 30, preferably a red laser, provides a collimated light beam 32 to a first cylindrical lens 34. The cylindrical lens 34 redirects the light into a "slit-like" beam 36 which comes to a horizontally aligned, line focus 38 on the center axis 18. The light, after passing through the line focus 38, is stopped by a beam dump 39. Scattered light, shown by light rays 41, is intercepted by a detector 42, preferably a photoelectric device. By virtue of this arrangement, the time of flight of each individual particle can be determined. More specifically, the leading end of the particle will initially scatter light, and the particle will continue to scatter light until the trailing end of the particle passes through the light beam. The line focus 38 is positioned just under the orifice 16, so that, if the particles are deformed, or are naturally elongated, the hydrodynamic forces are sufficiently strong to maintain alignment and deformation if any of the cell while passing through the line focus 38. The distance between the orifice 16 and the exit nozzle 27 is somewhat exaggerated in FIG. 1 so as to better illustrate the optical measurements. Although the impedance sensing and the optical detection are undertaken at different positions on the center axis 18, they could be measured simultaneously by using known light transparent flow cells. The electrical signal from the detector 42 is processed by pulse duration circuitry 43 of conventional construction, which obtains a desired signal representative of the time duration during which some part of the particle was in the beam 36, or to put it another way, its time of flight. Such circuitry is shown in U.S. Pat. No. 3,890,568 to Coulter et al. Since the velocities of the particles as they pass through the line focus 38 can be predetermined, a digital computer 44 can be used to correlate each particle's timer of flight with its length along its elongated axis.

The sample introduction tube 12, which is composed of a suitably conductive material, serves in the preferred embodiment as an upstream electrode for the impedance sensing orifice 16. The inlet tube 26 likewise is formed of a suitably conductive material and serves as a downstream electrode for the orifice 16. The sheath tube 14 is composed of a suitable non-conducting material. The orifice 16 is formed in a sapphire wafer 45 positioned at the end of the sheath tube 14. Since the orifice 16 provides the only fluid connection between the tube 12 and the tube 26, an electric field is established in the orifice 16. In a known arrangement, a low frequency current source 46 and a high frequency current source 48 are electrically coupled to the sample introduction tube 12 by a conductor 50 and to the inlet tube 26 by a conductor 52, which is held at ground potential. The low frequency current source 46 provides a "zero frequency" direct current or a current with a sufficiently low frequency that the reactive part of the particle impedance has a negligible effect on the response of the apparatus 10, given the typical times taken for the particle to pass the orifice 16. For the purpose of this application, a low frequency current source will be defined to include a direct current source. The only criterion is that the resultant signals attributable to the low frequency source, when the particles pass through the orifice 16, are primarily proportional to the size of the particle. The high frequency current source 48 provides a current through the orifice 16 simultaneously with the current from the source 46, which has a frequency in the radio spectrum or even higher. The two sources 46 and 48 each produce identifiable signals capable of separate detection when the particle moves through the orifice 16, one signal being a low frequency (L.F.) signal which is due almost completely to the size of the particles, and the other being a radio frequency (R.F.) signal (being defined as above 1 MHz) which is due not only to the size, but to the combined effects of size, shape, resistivity and reactance. These output signals are applied by the conductors 50 and 52 to a conventional detecting means 54. The detecting means 54 includes a detector 56 for the R.F. signals and a detector 58 for the L.F. signals, each of the detectors 56 and 58 receiving the signals through the conductors 50 and 52. A first impedance signal $S(LF)$, produced by the detector 58, is of a nature that primarily relates to the size of particles. The detector 58 typically includes amplifiers, filters, and other well known circuitry which commonly is found in a commercial Coulter Counter ®, with the addition of means, such as a low-pass filter, for preventing the R.F. signals from saturating the circuit. If the low frequency is not zero, then demodulating circuitry is included. The detector 56 includes amplitude modulation detection means for demodulating the R.F. signal to produce a pulse-type, second impedance signal S(RF). The detector 56 can include filters, amplifiers, demodulators and other known circuitry. The structures of the current sources 46 and 48 and the detecting means 54 are well known in the art and the detailed construction of these devices is provided in U.S. Pat. No. 3,502,974 to Coulter et al. and U.S. Pat. No. 3,502,973 to Coulter et al. The air-filled chamber 29 provides an air gap between the electrolyte solution upstream of the orifice 16 and the electrolyte solution downstream of the orifice 16, thereby reducing the high frequency current losses.

From the first impedance signal S(LF), the second impedance signal S(RF), and the time of flight signal t from the pulse duration circuitry 43, the computer 44 will digitize the signals, correlate the signals on a particle by particle basis and store the signals in memory. In the preferred embodiment, the optical signals are generated at a location below the location at which the impedance signals are produced. Hence, there is a time delay between when the earlier-produced first and second impedance signals are produced and when the length signal is produced. The data storage capability of the digital computer 44 readily accounts for this time delay and allows the three signals to be correlated for each of the particles. Alternatively, hardwired circuitry can be used to provide delay means for the impedance signals to allow for the three signals to be correlated, as shown by U.S. Pat. No. 3,976,862 to Curbelo. For better visualization of the calculations made by the computer 44, the computer 44 is divided into a first memory, collating, and calculating means 60 and a second memory, collating, and calculating means 62. A hardwired electrical circuit version of the computer 44 is possible, and would have these separate units. However, it is preferable to use the digital computer 44 with stored program control. The calculating means 60 receives the impedance signal S(LF) and the time of flight signal t and, from these signals, takes into account the shape of each particle and modifies the impedance signal S(LF) to obtain a true or actual volume measurement $v_p$ and a ratio measurement of each particle's length to width (a/b). The calculating means 60, which does not require the impedance signal S(RF), generates a useful output itself, since the impedance signals S(LF) can be corrected to reflect the true volume $v_p$ and the length to width ratio a/b correlates with particle deformation. Moreover, the invention provides novel optical detector means, utilizing the slit-like beam 36, for determining the time of flight signal t. The means 60 also calculates a shape factor f from the time of flight signal t and the impedance signal S(LF) and passes it on to the calculating means 62. The means 62 receives a novel combination of signals for each particle, consisting of the impedance signal S(RF), the impedance signal S(LF), and a shape factor f, which in turn has been calculated from the impedance signal S(LF) and time of flight signal t in the means 60. The means 62 digitizes the signals, correlates the signal on a particle-by-particle basis, and stores the signals in memory. From the unique combination of all three input signals, the means 62 can calculate the internal resistivity $\rho_i$ on a particle-by-particle basis. A collating means 64 correlates the true volume measurement $v_p$, the ratio measurement a/b and the internal resistivity $\rho_i$ for each individual particle and a readout means 66 prints and/or displays the accumulated data. The mathematics for making the above calculations will follow.

While the present invention is intended to cover particles in general, more specifically, the term particles includes membrane-sheathed particles which we will term cells. The cells can be, for example, biological cells or artifical membrane-sheathed cells.

FIG. 2 represents a known circuit diagram for modeling the electrical characteristics of a cell and its surrounding suspension liquid and is presented herein only as an analog to aid in understanding. The cell is shown by a dash outline 68. The various electrical resistance values R in ohms, to be described hereinafter, are related to the electrical resistivity values $\rho$ of the specified materials or solutions by well known equations. The resistivity $\rho$, which is the reciprocal of conductivity $\sigma$, is generally measured in ohm-centimeters. The resistivity value of $\rho_e$, $\rho_m$, and $\rho_i$ designate the resistivity of the electrolyte suspension liquid surrounding the cell, the membrane of the cell and the internal constitutents of the cell, respectively. Hence, a circuit 70 comprises a series circuit of a resistance R1($\rho_e$), resistance R2($\rho_e$) and resistance R3($\rho_e$), each representing a portion of the suspending liquid. In parallel with the resistance R2($\rho_e$) is a circuit 72 representing the cell. The circuit 72 twice includes in series the impedance of the cell's membrane, shown by the parallel arrangement of a resistance R4($\rho_m$) and a capacitance C1, and by a resistance R5($\rho_m$) and a capacitance C2, the two impedances being assumed to be equal. Interposed in series between these two impedances is an internal resistance R6($\rho_i$). This internal resistance R6($\rho_i$) has been found to be important for examining cells. The predetermined trajectory 74 is shown aligned with the elongated axis of the cell. In the embodiment illustrated in FIG. 1, the predetermined trajectory would be along the center axis 18. The current flow is assumed to be parallel with the predetermined trajectory 74. For the purposes of illustration, now imagine the cell being rotated. If the cell possesses an elongated axis and if the axis is progressively angled with respect to the predetermined trajectory 74, the internal resistance R6($\rho_i$) progressively decreases. Hence, it has been found that in order to compare resistance value R6($\rho_i$) of different cells, the orientation of the cells must be the same for each cell at the time of measurement. From the above concepts taken from an analog model which will not be developed any further here, the measurement of the cellular resistivity $\rho_i$ depends upon the cell's shape and orientation. Therefore, the true cell shape must be determined and the orientation maintained in order to calculate the internal resistivity of the cell from the measured parameters. This is made more difficult by the fact that the membrane resistivity $\rho_m$ is much greater in magnitude than the internal resistivity $\rho_i$, although the internal resistivity $\rho_i$ is typically greater in magnitude than the liquid resistivity $\rho_e$. Due to the unique combination of signal the apparatus 10, the internal resistivity $\rho_i$ can be determined on a cell by cell basis. A discussion of the mathematics for determining the internal resistivity $\rho_i$, or its inverse counterpart, internal conductivity $\sigma_i$, will be discussed hereinafter.

As will become evident, if the shape factor f can be determined, the internal resistivity $\rho_i$, or its inverse counterpart conductivity $\sigma_i$, can be determined. In addition the impedance signal S(LF) can be corrected to reflect the true volume $v_p$. The impedance signal S(LF) is related to the true volume $v_p$ by the shape factor f in the following equation:

$$S(LF) = f \cdot v_p \cdot E(LF) \qquad (1)$$

The impedance signal S(RF) is related to the true volume $v_p$ by the shape factor f in the following equation:

$$S(RF) = f \cdot v_p \cdot \frac{(1 - \rho_e/\rho_i) \cdot E(RF)}{1 + (\rho_e/\rho_i) \cdot (f - 1)} \qquad (2)$$

The opacity Op is obtained as follows:

$$Op = \frac{S(RF)}{S(LF)} = \frac{(1 - \rho_e/\rho_i) \cdot E(RF)}{[1 + (\rho_e/\rho_i) \cdot (f - 1)] \cdot E(LF)} \qquad (3)$$

The following presentation describes a method to derive equations (1) and (2). The particle is assumed to have a prolate ellipsoidal configuration. Next, Laplace's equation is solved in ellipsoidal coordinates for the particle, with the long axis of the simulated ellipsoidal particle being defined as the coordinate axis z, with the z axis being parallel to the electrical field and current flow in the orifice. First, Green's theorem, which gives a volume integral in terms of a surface integral, can be written as follows, where there is no charge present:

$$\oint_S \left( \phi \cdot \frac{dz}{dn} - Z \cdot \frac{d\phi}{dn} \right) \cdot ds = 0 \qquad (4)$$

where $\phi$ is the bounded potential distribution external to the particle and n is a vector outward normal to the surface s. Next, the surface of the orifice 16 is integrated to give the following surface integral:

$$\oint_O = \frac{\Delta R}{R} \cdot E \cdot v_o = S(E) \cdot v_o \qquad (5)$$

where $\Delta R$ is the change in the orifice resistance R when a particle is present, E is the electric field strength at any point inside of the orifice, $v_o$ is the effective orifice volume, and S(E) is the measured impedance signal. The potential over the surface of the particle can be given by the solution of Laplace's equation with the boundary conditions that there is a potential across the membrane and current continuity through the membrane. Hence, the following relationships exist:

$$\phi = [-E \cdot F(\xi_1) + \alpha_1 \cdot G(\xi_1)] \cdot \frac{1}{A_1} \cdot F(\xi_2) \cdot F(\xi_3) \qquad (6)$$

where $\xi_1$, $\xi_2$, and $\xi_3$ are ellipsoidal coordinates. The other terms of the above equation are defined as follows:

$$F(\xi_1) = (\xi_1 + a^2)^{\frac{1}{2}} \qquad (7)$$

$$A_1 = [(b^2 - a^2) \cdot (c^2 - a^2)]^{\frac{1}{2}} \qquad (8)$$

$$G(\xi_1) = \frac{3}{2} \cdot F(\xi_1) \cdot \int_{\xi_1}^{\infty} \frac{du}{F(u) \cdot R(u)} \qquad (9)$$

$$R(u) = [(u + a^2) \cdot (u + b^2) \cdot (u + c^2)]^{\frac{1}{2}} \qquad (10)$$

where a, b, and c are the semi-long, semi-short, and semi-short axis of the prolate ellipsoid, respectively. The term u is a generalized coordinate. The term $\alpha_1$ is equal to the surface integral of the particle, divided by $4\pi$, yielding:

$$\oint_P = 4\pi\alpha_1 \qquad (11)$$

$\alpha_1$ in turn is defined by applying appropriate boundary conditions upon the description of the potential internal and external to the cell.

$$\alpha_1 = \frac{-f \cdot v_p}{4\pi} \cdot \left[ \frac{(1 - \rho_e/\rho_i) \cdot E + (\rho_e/\rho_i) \cdot (V_m^o/a)}{1 + (\rho_e/\rho_i) \cdot (f - 1)} \right] \qquad (12)$$

$$\oint_S = \oint_O + \oint_P = 0 \qquad (13)$$

$$S(E) = f \cdot \left( \frac{v_p}{v_o} \right) \cdot \left[ \frac{(1 - \rho_e/\rho_i) E + (\rho_e/\rho_i) \cdot (V_m^o/a)}{1 + (\rho_e/\rho_i) \cdot (f - 1)} \right] \qquad (14)$$

$$\frac{1}{f - 1} = \frac{1 - \frac{a \cdot b \cdot c}{2} \int_0^\infty \frac{du}{F^2(u) \cdot R(u)}}{\frac{a \cdot b \cdot c}{2} \int_0^\infty \frac{du}{F^2(u) \cdot R(u)}} \qquad (15)$$

where $\rho_i$ and $\rho_e$ are the internal and external resistivities of the cell respectively, $V_m^o$ is the membrane (designated by subscript "m") potential at the poles (designated by superscript "o") of the ellipsoid aligned with the current direction. Now, the limiting conditions for the equation (14) must be examined. The first limiting condition is the application of the low frequency current source 46 which produces in the orifice 16 an electrical field (E(LF)). This leads to the following results:

$$V_m^o = f \cdot a \cdot E(LF) \qquad (16)$$

where S(E) = S(LF) and E = E(LF).
Consequently:

$$S(LF) = f \cdot (v_p/v_O) \cdot E(LF) \qquad (17)$$

Referring to FIGS. 1 and 2, this first limiting condition means that, for the application of the low frequency current source 46, the capacitance C1 and C2 provide such high impedances that they substantially act as open circuits. Hence, the internal resistance of a cell is not detectable due to the high resistivity of the cell's membrane. Now, the second limiting condition for equation (14) is the application of the high frequency current source 48, which produces in the orifice an electric field E(RF). If the frequency is high enough, for instance 30 MHz, this leads to the following results:

$$V_m^o = O \qquad (18)$$

where S(E) = S(RF) and E = E(RF).
Consequently:

$$S(RF) = f \cdot \left(\frac{v_p}{v_o}\right) \cdot \left[\frac{(1 - \rho_e/\rho_i) \cdot E(RF)}{1 + (\rho_e/\rho_i) \cdot (f - 1)}\right] \quad (19)$$

Referring to FIGS. 1 and 2, this second limiting condition means that for the application of the high frequency current source 48, the capacitance C1 and C2 substantially short circuit to act as shunts about the very high membrane resistances. Consequently, the internal resistivity of the cell is measured readily. Now opacity is calculated, leading to the following relationship:

$$O_p = \frac{S(RF)}{S(LF)} = \left[\frac{(1 - \rho_e/\rho_i) \cdot E(RF)}{(1 + (\rho_e/\rho_i) \cdot (f - 1)) \cdot E(LF)}\right] \quad (20)$$

With reference to equation (20), all the variables are known, except the shape factor f and the internal resistivity $\rho_i$. Hence, if the shape factor f can be determined, the internal resistivity $\rho_i$ can be calculated. This can be accomplished by the development of the following relationships. The true volume $v_p$ of the cell and the length a are related to the shape factor f, where the semi-short axis b and c are equal, by the following equations:

$$b = \left(v_p \cdot \frac{3}{4\pi} \cdot \frac{1}{a}\right)^{\frac{1}{2}} \quad (21)$$

$$m = \frac{a}{b} \quad (22)$$

$$f - 1 = \frac{m^2}{m^2 - 1} - \frac{m \cdot \cosh^{-1} m}{(m^2 - 1)^{3/2}} \text{ for } m > 1 \quad (23)$$

Consequently, equations (17) and (23) provide two non-linear simultaneous equations to solve for the shape factor f and the true volume $v_p$. The calculations to obtain these two terms can be accomplished with just the impedance signal S(LF) and the time of flight t, which provides the particle length a. Equation (21) assumes that the particle has an ellipsoidal shape. As shown in FIG. 1, the shape factor f and the true volume $v_p$ are calculated in the calculating means 60. Having solved for the shape factor f, equation (20) can be solved by the calculating means 62 to find the internal resistivity $\rho_i$ on a cell-by-cell basis. This calculation requires the receipt of the impedance signal S(RF), impedance signal S(LF) and the shape factor f.

An alternative way of electronically obtaining the length of an elongated axis of the particles is disclosed in the U.S. Pat. No. 3,793,587 to Thom et al. and is incorporated by reference herein. Although the present invention includes novel optical detection means for obtaining the particles length, the same length determination can be made, albeit with less accuracy, by the two orifice arrangement of the Thom patent. Having obtained the particle's length by known electronic detection means or by novel optical electronic detection means, a novel combination of signal inputs, consisting of the impedance signal S(LF), the impedance signal S(RF) and the particle's length, allows for the determination of the cells internal resistivity $\rho_i$. One of the two orifices of the Thom patent has an axial length of the same order of magnitude of the particle lengths or smaller than the particle lengths. The duration of the pulse created by the particle correlates with the particle length. Hence, when the phrase "detection means" for determining particle length is used in the claims, it is intended to cover optical detection means, such as the use of the slit-like beam 36, and also electronic detection means, such as the orifice of the Thom patent, which has a short axial length.

The electrical changes caused by the particles will occur within the effective confines of the orifice 16, defined as a sensing zone or scanning ambit. As described in detail in U.S. Pat. No. 3,890,568 to Coulter et al., the sensing zone extends substantially beyond the axial length of the orifice 16. For the purposes of this application, the sensing zone will be defined to include the region around the orifice 16 wherein the electric field intensity is at least one percent or more of that in the central region inside the orifice 16.

It is to be understood the flow arrangement having flow chamber 20, as depicted in U.S. Pat. No. 3,710,933 to Fulwyler et al., represents only one of many possible flow arrangements that can be used to practice the present invention, and the invention is not limited to this structure. It is contemplated that this invention can be used with any flow-through arrangement wherein particles are hydrodynamically focused to pass through an impedance sensing orifice.

Although particular embodiments of the invention have been shown and described here, there is no intention to thereby limit the invention to the details of such embodiments. On the contrary, the intention is to cover all modifications, alternatives, embodiments, usages and equivalents of the subject invention as fall within the spirit and scope of the invention, specification and the appended claims.

What is claimed is:

1. A particle scanning apparatus including an orifice for electrical impedance measurements of individual particles suspended in a liquid stream, focusing means for hydrodynamically focusing the stream of particles so the particles proceed along a predetermined trajectory through the orifice, first electrical current means for providing a low frequency electrical current through said orifice to produce an electrical first impedance signal for each particle, second electrical current means for providing a high frequency electrical current through said orifice to produce an electrical second impedance signal for each particle, the particle scanning apparatus comprising:

detection means for producing a length signal representative of the length of each particle;

means for correlating said length signal, said first impedance signal and said second impedance signal for each particle;

whereby the producing and correlating of said signals provides all the parameters required for the determination of the internal resistivity of each particle.

2. The particle scanning apparatus of claim 1, further including, calculating means for calculating the internal resistivity of each particle from said first impedance signal, said second impedance signal, and said length signal for that particle.

3. The particle scanning apparatus of claim 1, wherein said detection means includes means for detecting the presence of a particle within a predetermined region, which is disposed along said predetermined trajectory where the particle is hydrodynamically focused, and further includes means for providing a duration signal representative of the duration of the passage of the particle through said predetermined region, whereby said duration signal represents the length of the particle.

4. The particle scanning apparatus of claim 1, wherein said detection means comprises a radiation source for providing a narrow beam of radiation to intercept the particle while the particle is hydrodynamically focused and means for measuring the duration of the passage of the particle through said narrow beam.

5. The particle scanning apparatus of claim 1, wherein said particles comprise cells.

6. The particle scanning apparatus of claim 1, wherein said first electrical current means provides said current therefrom with a sufficiently low frequency that said first impedance signal is primarily representative of the particle's size and said second electrical current means provides said current therefrom with a sufficiently high frequency that said second impedance signal is representative of the particle's internal resistivity, size and shape.

7. A particle scanning apparatus including an orifice for impedance measurements of individual particles suspended in a liquid stream, focusing means for hydrodynamically focusing the stream of particles so the particles proceed along a predetermined trajectory through said orifice, first electrical current means for providing a low frequency electrical current through said orifice to produce an electrical first impedance signal, said particle scanning apparatus comprising:

optical detection means for providing a narrow beam of radiation to intercept each particle while the particle is hydrodynamically focused and for providing a duration signal representative of the duration of the passage of the particle through said narrow beam, whereby said duration signal represents the particle's length;

means for correlating said duration signal to the corresponding said first impedance signal for each particle;

whereby producing and correlating said signals provides all the parameters required for calculations to determine particle shape factor, to correct a size measurement based upon said first impedance measurement to account for particle shape, and to determine the shape of a particle.

8. The particle scanning apparatus of claim 7, further including, calculating means for calculating the shape factor from said first impedance signal and said duration signal for each particle.

9. The particle scanning apparatus of claim 7, further including, calculating means for correcting a size measurement based upon the first impedance signal to account for particle shape, so as to give a true volume measurement for each particle.

10. The particle scanning apparatus of claim 7, further including, calculating means for calculating the ratio of the length and the width of the particle, whereby said ratio provides an indicator of the shape of the particle.

11. The particle scanning apparatus of claim 7, further including, second electrical current means for providing a high frequency electrical current through the orifice to produce a second electrical impedance signal;

means for correlating the first impedance signal, the second impedance signal and the duration signal for each particle for the determination of the internal resistivity of each particle.

12. The particle scanning apparatus of claim 7, wherein the particles comprise cells.

13. A particle scanning method wherein individual particles, suspended in a liquid stream, are hydrodynamically focused to pass through an orifice for measuring electrical impedance, a low frequency electrical current passes through the orifice to produce an electrical first impedance measurement, a high frequency electrical current passes through the orifice to produce an electrical second impedance measurement, the method comprising:

measuring the length of each particle while the particle is hydrodynamically focused;

correlating the first impedance measurement, the second impedance measurement and the length measurement for each particle and calculating therefrom the internal resistivity of each particle.

14. The method of claim 13, wherein said particles are cells.

* * * * *